United States Patent
Poezevera

(10) Patent No.: US 7,395,115 B2
(45) Date of Patent: Jul. 1, 2008

(54) DETECTION AND THE TREATMENT OF VENTILATORY DISORDERS DURING SLEEP FOR AN ACTIVE IMPLANTABLE MEDICAL DEVICE, IN PARTICULAR A PACEMAKER

(75) Inventor: Yann Poezevera, Courcouronne (FR)

(73) Assignee: Ela Medical S.A.S., Montrouge (FR)

( * ) Notice: Subject to any disclaimer, the term of this patent is extended or adjusted under 35 U.S.C. 154(b) by 386 days.

(21) Appl. No.: 10/364,293

(22) Filed: Feb. 10, 2003

(65) Prior Publication Data
US 2004/0006375 A1 Jan. 8, 2004

(30) Foreign Application Priority Data
Feb. 15, 2002 (FR) ................................ 02 01936

(51) Int. Cl.
*A61N 1/365* (2006.01)
(52) U.S. Cl. ............................. 607/20; 607/9
(58) Field of Classification Search ................ 600/484, 600/17, 26; 607/20
See application file for complete search history.

(56) References Cited

U.S. PATENT DOCUMENTS

| | | | | |
|---|---|---|---|---|
| 4,901,725 A * | 2/1990 | Nappholz et al. | ............. | 607/17 |
| 5,303,702 A | 4/1994 | Bonnet et al. | ................. | 607/20 |
| 5,485,851 A * | 1/1996 | Erickson | ...................... | 600/529 |
| 5,622,428 A | 4/1997 | Bonnet | ....................... | 128/630 |
| 5,704,345 A * | 1/1998 | Berthon-Jones | ........ | 128/204.23 |
| 5,722,996 A | 3/1998 | Bonnet et al. | ................. | 607/17 |
| 5,766,228 A | 6/1998 | Bonnet et al. | ................. | 607/16 |
| 6,015,388 A | 1/2000 | Sackner et al. | .............. | 600/529 |
| 6,126,611 A * | 10/2000 | Bourgeois et al. | ........... | 600/529 |
| 6,574,507 B1 * | 6/2003 | Bonnet | ........................ | 607/20 |
| 6,589,188 B1 * | 7/2003 | Street et al. | ................. | 600/538 |

FOREIGN PATENT DOCUMENTS

| EP | 0 493 222 A1 | 7/1992 |
|---|---|---|
| EP | 0 702 977 A2 | 3/1996 |
| EP | 1 151 718 A2 | 11/2001 |

OTHER PUBLICATIONS

"Definition of Apnea", MedTerms Medical Dictionary, http://www.medterms.com/script/main/art.asp?articlekey=2309.*
"Breathing—slowed or stopped", MedlinePlus Medical Encyclopedia, http://www.nlm.nih.gov/medlineplus/ency/article/003069.htm.*

* cited by examiner

*Primary Examiner*—George Robert Evanisko
*Assistant Examiner*—Michael Kahelin
(74) *Attorney, Agent, or Firm*—Orrick Herrington & Sutcliffe, L.L.P.

(57) ABSTRACT

An active medical device that is able to detect and treat ventilatory activity disorders during sleep. This device measures the patient's respiratory activity, delivers a signal of the ventilatory activity of the patient, analyzes the ventilatory activity signal, and detects the occurrence of hypopneas. The analysis includes calculating at regular intervals a sliding average of the signal of ventilatory activity, comparing the values of the successive sliding averages thus calculated, and detecting an occurrence of an hypopnea when, for two successive sliding averages, the difference between the averages crosses a predetermined threshold of comparison. When the device is one that also delivers cardiac stimulation pulses, it is advantageously envisaged to modify an operating parameter, in particular the stimulation rate based on the detected hypopnea, to treat the hypopnea.

15 Claims, 2 Drawing Sheets

DETECTION AND THE TREATMENT OF VENTILATORY DISORDERS DURING SLEEP FOR AN ACTIVE IMPLANTABLE MEDICAL DEVICE, IN PARTICULAR A PACEMAKER

FIELD OF THE INVENTION

The present invention relates to "active medical devices" as such devices are defined by the Jun. 14, 1993 Directive 93/42/CEE of the Council of the European Communities, and more particularly to the diagnosis of respiratory disorders that occur during the sleep, and the control of heart rate at the time of the possible waking-up. Although described in the case of implantable active medical devices, such as cardiac pacemakers, defibrillators and/or cardiovertors that are able to deliver to the heart low energy pulses for treating disorders of the heartbeat rate, it should be understood that the invention is not limited to such implantable active medical devices, but is rather directly applicable to many types of diagnostic and/or therapeutic active medical devices.

BACKGROUND OF THE INVENTION

In this context, one device already proposed allows one to diagnose various respiratory disorders, such as apnea, revealing a pathology known by the name of Syndrome of Sleep Apnea ("SSA"). Such an apnea is defined as a respiratory pause of a duration longer than ten seconds, and occurring during a phase of sleep of the patient. SSA can also be defined by a significant recurrence of hypopneas. One can also detect disorders revealed by a periodic and abnormal variation of the respiratory profile, where phases of hyperventilation alternate with either phases of normal breathing or phases of hypoventilation, a disorder known by the name of "Periodic Breathing ("PB"), or respiratory pause phases (a disorder known by the name of "Cheyne-Stokes dyspnea" or "Cheyne-Stokes breathing", or Cheyne-Stokes Respiration ("CSR")). The various alternate phases each have a duration of a few respiratory cycles to a few tens of respiratory cycles, i.e., of a few seconds or tens of seconds, and in some circumstances in excess of a minute.

Cardiac pacemakers including means for measuring the respiratory activity of the patient, more precisely the minute-ventilation (i.e., the product of the respiratory frequency by the ventiliatory amplitude) are known from, for example, European Patent Publication EP-A-0 493 222 and its corresponding U.S. Pat. No. 5,303,702, assigned to the assignee hereof Ela Médical. However, the minute ventilation parameter is disclosed in that document to control the frequency of application of the stimulation pulses, but not to carry out an analysis of the ventilation able to detect some particular disturbance occurring during sleep.

The starting point of the invention lies in the observation of the existence of respiratory disorders occurring during sleep, the symptoms of which are neither respiratory pauses nor periodic variations of the ventilatory profile. These disorders can nevertheless-induce, in particular, an oxygen desaturation of the blood that is likely to cause the patient to wake up, and further, especially, a transitory sinusal tachycardia intended for compensating the desaturation. Those disorders are called "hypopneas" (as defined below).

OBJECTS AND SUMMARY OF THE INVENTION

It is, therefore, an object of the present invention to propose a device that can detect this type of disorder during the sleep of the patient.

It is another object of the present invention to propose a device including a mode of therapy, in particular the delivery of cardiac stimulation pulses, that is able to modify one of its operating parameters, for example, the stimulation rate, when such a disorder is detected and certain specific criteria are fulfilled, so as to anticipate and avoid the consequences of the disorder, and in particular to avoid waking-up the patient and the anomalies of the heartbeat rate as a consequence of the oxygen desaturation.

Broadly, the present invention is directed to an active medical device including means for measuring the respiratory activity, able to deliver a signal corresponding to the ventilatory activity of the patient, and means for analyzing the ventilatory signal and detecting the occurrence of hypopneas. A "hypopnea" is defined as a significant decrease of the minute-ventilation parameter, for example, more than 50%, compared to an average of prior reference values acquired. A hypopnea is distinguished from an apnea and a respiratory. pause, which are temporary stops of the respiratory function. In addition, a hypopnea within the meaning of the invention can occur in a sporadic manner, independently of other disorders of the respiratory profile such as PB or CSR as mentioned above, which are specific disorders that presuppose the existence of an alternation of phases of hyperventilation and phases of normal or reduced respiratory activity, but always in the form of a cyclic disorder.

One aspect of the invention is directed to a device is of the known type according to the above mentioned EP-A-0 493 222 and U.S. Pat. No. 5,303,702, i.e., that is able to analyze the ventilatory activity signal and detect hypopneas therefrom.

Very advantageously, the means for analyzing the ventilatory activity signal includes means for calculating at regular intervals sliding averages of measures of the signal of ventilatory activity, means for comparing the successive sliding averages thus calculated, and means for detecting the occurrence of an hypopnea, when, for two successive sliding averages, the difference between these averages crosses a predetermined threshold of comparison. The sliding averages can be calculated based upon a predetermined time interval or upon a predetermined number of respiratory cycles N, with N≧1. The time intervals, or the numbers of cycles N, over which the successive sliding averages to be compared are calculated, can be the same for the two values to be compared, or they can be different.

Preferably, the means for analyzing also comprises means, responsive to an occurrence of a hypopnea, for determining the duration of the hypopnea thus detected. One such duration determining means can be a counter for counting:

(i) the number of consecutive respiratory cycles for which the average of the ventilatory activity signal remains below the predetermined threshold of comparison of the last non-hypopneic average, or (ii) the number of calculation periods of the sliding averages for which the average of the ventilatory activity signal remains below the predetermined threshold of comparison of the last non-hypopneic average.

The "last non-hypopneic average" is the sliding average that was last acquired that, when compared to its preceding sliding average, was determined not to be hypopneic.

More preferably, the device also has an operating control means that is able to modify an operating parameter of the device in the event of the occurrence of hypopneas detected by the analyzing means. The modification of the operating parameter can be operated when the accumulated duration of hypopneas measured over a given period is greater than a predetermined threshold, or when the number of hypopneas measured over a given period is greater than a predetermined threshold.

When the device also comprises means for delivering cardiac stimulation pulses, the aforementioned operating parameter is very advantageously the stimulation rate, and the operating control means operates to increase the stimulation rate in the event of an occurrence of hypopneas detected by the analyzing means.

Preferably, the device further comprises means for detecting the awakening and sleep phases of the patient activity, and the means for analyzing are also able to correlate the modifications of the aforesaid operating parameter with the consecutive transitions from a phase of sleep towards a phase of awakening, and to deliver an indicator in the event of a correlation thus detected, typically in the event of the occurrence of a transition in a given time interval following a modification of the operating parameter.

Advantageously, it also is contemplated that the means for operating a modification of the operating parameter can modify the operating parameter in a reverse direction in response to the delivery of an indicator of correlation by the analyzing means, in particular when the number of delivered indicators of correlation attains a predetermined level. In an embodiment in which the device comprises means for delivering cardiac stimulation pulses and the operating parameter is the stimulation rate, the means for operating a modification of the aforesaid operating parameter in the reverse direction operates to decrease the stimulation rate below the level it was increased to when the hypopneic condition was first determined, the reduction being implemented for as long as the value of stimulation rate does not cross, i.e., fall below a predetermined base stimulation rate, more preferably, a rate slightly above the patient's resting or base stimulation rate.

In addition, the means for analyzing also are advantageously able to determine a phase of a respiratory pause and to discriminate between phases of respiratory pauses and phases of hypopneas, and to suspend the determination of the duration of hypopnea during a determined phase(s) of respiratory pauses.

BRIEF DESCRIPTION OF THE DRAWING

Further benefits, features and characteristics of the present invention will become apparent to a person of ordinary skill in the art in view of the following detailed description of the invention, made with reference to the annexed drawings, in which.

DETAILED DESCRIPTION OF THE INVENTION

As indicated above, the respiratory pause is not the only sleep disorder that induces a blood oxygen desaturation. The significant reduction (without a respiratory pause) of the respiratory volume, or hypopnea, is another cause of desaturation. The invention thus proposes to detect the occurrence of such hypopneas by an analysis of the variation of the ventilatory activity, specifically the minute-ventilation signal.

The minute-ventilation signal, in a well-known manner, is measured starting from the parameters of amplitude and periodicity of the successive respiratory cycles. The cycle to cycle analysis is carried out according to a standard known technique, for example, as described in EP-A-0 493 222 and U.S. Pat. No. 5,303,702 mentioned above, to which one will be able to refer for further details regarding a representative technique by which the signal representative of the respiratory activity is collected and analyzed, in particular to obtain the information from minute-ventilation (signal called "VE" or "MV"). The disclosure of U.S. Pat. No. 5,303,702 is incorporated herein by reference in its entirety.

Signal MV is a parameter of physiological preponderance that is preferably obtained by an intrathoracic impedance measurement. This measurement is operated between two electrodes placed on or in the rib cage, or between an electrode (for example, a stimulating electrode if the device is an implanted one such as a cardiac pacemaker) and the case of the device. The impedance is measured by injection of a constant current of a few hundred microamperes, at a frequency of a few Hertz, typically 8 Hz, and detection of a voltage signal representing the intrathoracic impedance and corresponding to ventilatory activity. One can determine from this voltage signal a respiratory period defined as the lapse of time separating two peaks of the impedance signal. The peaks correspond to high impedances obtained at the time of the inspiration (when the lungs are filled with air). The decrease of the impedance corresponds to an expiratory phase. This technique, for example, is described by Bonnet J L et al., "Measurement of Minute-Ventilation with Different DDDR Pacemaker Electrode Configurations", *PACE*, Vol. 21, 98, Part 1, and it is implemented in the commercial cardiac pacemaker device sold under the trade names CHORUS RM 7034™, TALENT™ and SYMPHONY™ by ELA Médical.

It will, however, be understood by persons of ordinary skill in the art that the invention is not limited to only those devices that perform an analysis of a physiological signal of minute-ventilation, although it is the most current configuration and, for this reason, the present description will be made within the framework of this example. Thus, the invention applies as. well to devices implementing other types of physiological sensors such as pH sensors, blood oxygen saturation sensors, etc.

Figure 1:
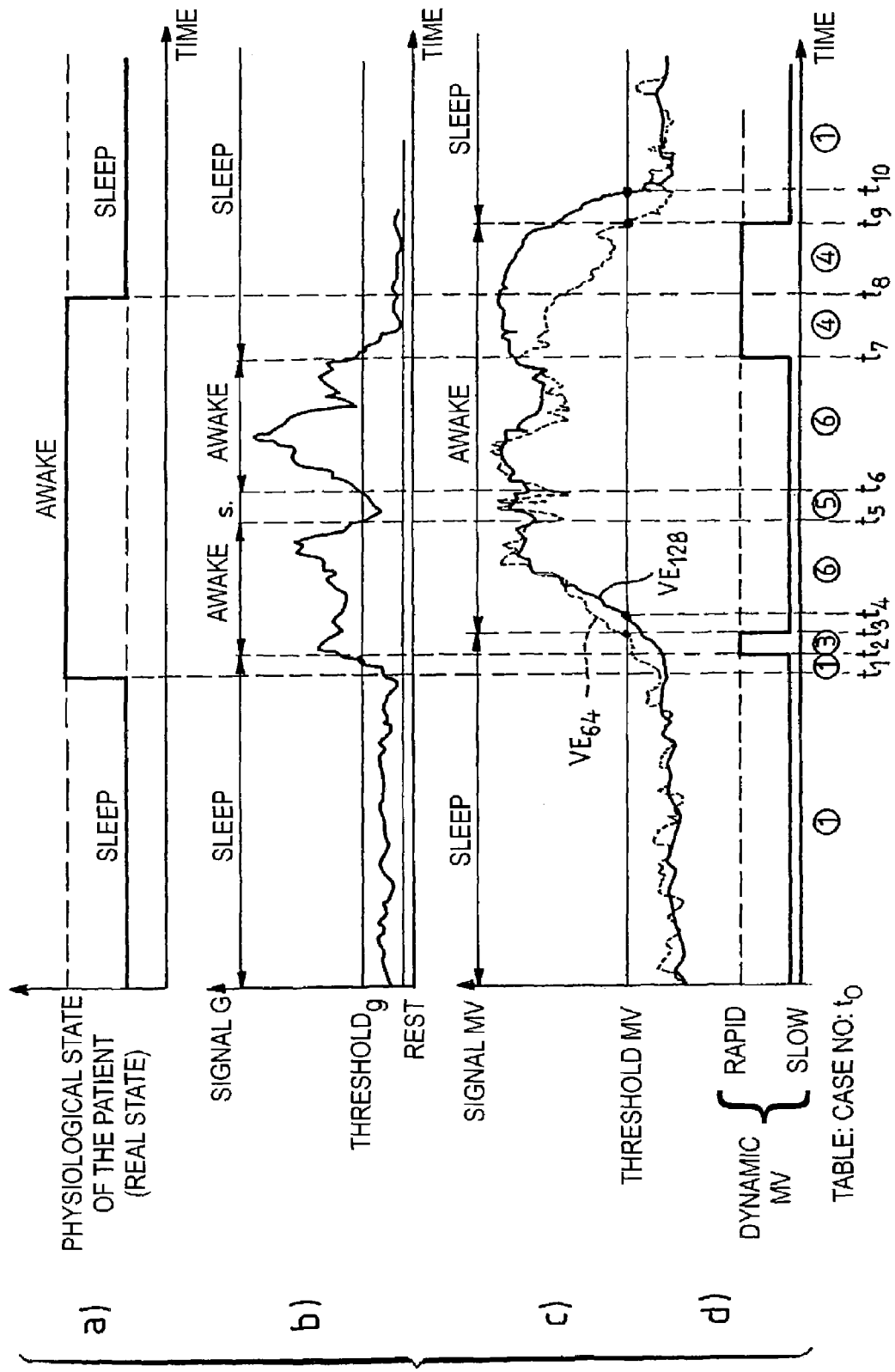
FIG. 1 is a flow chart of a process by which hypopneas are detected and analyzed to determine whether a control parameter, e.g., stimulation rate, should be modified.

Referring to FIG. 1, to detect a hypopnea, the device compares sliding averages of the minute-ventilation, for example, averages established over a duration T, e.g., T=10 seconds (step 110). If, between two consecutive averages, a significant decrease of the minute-ventilation is detected, for example, a decrease of more than 50% (step 120), then the device counts that decrease as one hypopnea (step 130).

In an alternative embodiment, the device can establish an average of the minute-ventilation on, for example, N' consecutive cycles where N'=4, and compare this value with the average of, for example, N preceding cycles where N=4 (i.e., the average is established over a given number of respiratory cycles, instead of being established based on a predetermined time interval).

It should be understood the intervals of time, or the numbers of cycles, over which the averages are calculated can be the same for the two averages to be compared—as in the example above—or can be different intervals. One can thus, for example, compare the average of the two last values of signal MV (N=2) with the average of the four preceding values) ($N^1$=4), or compare the last value of signal MV (N=1) with the average of the four preceding values ($N^1$=4). In this last case, the "average" is obtained starting from a single value. In other words, the concept of an "average of N values" is taken in the broad sense with $N \geq 1$ and $N^1 \geq 1$.

The device also determines the duration of a detected hypopnea (step 130), which duration will be equal to the number of consecutive sliding periods (or to the number of consecutive cycles used to compile the average in the embodiment mentioned above) for which the value of the minute-ventilation will remain lower than the threshold of comparison of the last non-hypopneic average. In the event of the occurrence of one or more hypopneas, when certain criteria are fulfilled, the device modifies an operating parameter (step 140). For a pacemaker type device, the operating parameter typically modified is the stimulation rate, the frequency of delivery of the stimulation pulses. The criteria conditioning the modification of the operating parameter can be in particular: (i) the cumulative duration of hypopneas measured over a given period (for example, over one hour) being greater than a threshold (for example, greater than 10 minutes); (ii) the number of hypopneas measured over a given period (for example, over one hour) is greater than a given threshold (for example, greater than 20); or (iii) the duration of a single hypopnea being greater than a predetermined threshold (for example, greater than 2 minutes) (step 140).

In one or the other of these cases, an oxygen desaturation is suspected, and the operating parameter is modified whereby the stimulation rate is accelerated (step 150). The acceleration may be a suitable amount for the given patient, preferably an increase of 15 to 20 bpm or an increase of 20% of the spontaneous cardiac rate. The acceleration of the heart rate is provided to increase the cardiac flow, while avoiding waking-up the patient and a possible sinusal tachycardia—the two principal consequences of the oxygen desaturation induced by the ventilatory disorder. However, it is possible that the acceleration of the heart rate by stimulation is too great and causes a systematic waking-up of the patient. To prevent such a situation from being repeated, and thus losing all the benefit of the treatment, the device analyzes the possible waking-up following an increase in stimulation rate.

Various techniques to operate an discrimination between awakening and sleep states are known. EP-A-0 719 568 and the corresponding U.S. Pat. No. 5,622,428 assigned herewith to Ela Médical, the disclosure of which is incorporated herein by reference, operates such a discrimination by an analysis of the minute-ventilation signal. An average signal MV is calculated over a given number of respiratory cycles, for example, the last 128 cycles, and compared to a reference value, for example, the average of signal MV over the last 24 hours. One can also use a sensor with a fast time response, typically an activity sensor or acceleration sensor ("sensor G"), whose signal makes it possible to detect physical movements of the patient. The information of this type of sensor is not in itself very specific with respect to distinguishing phases of awakening and sleep, but one can combine the signals delivered by a sensor G and a sensor MV to deduce some meaningful information, as described, for example in EP-A0 750 920 and its counterpart U.S. Pat. No. 5,722,996 also assigned to Ela Médical and EP-A0 770 407 and its counterpart U.S. Pat. No. 5,766,228 assigned to Ela Médical) to which one will be able to refer for further details, the disclosures of which U.S. patents are incorporated herein by reference.

An alternative technique for distinguishing the patient's sleep and awakening phases is disclosed in copending and commonly assigned U.S. patent application Ser. No. 10/310, 689 The disclosure, which is incorporated herein by reference in its entirety, and in particular for one suitable manner of determining whether the patient is in a sleep state or an awakening state, or transitioning therebetween. In this regard, the period of sleep is detected in an automatic manner, either starting from the signal delivered by the minute ventilation sensor MV, or by a separate sensor, for example, a sensor of patient activity measuring a parameter that is preponderantly physical, having a faster variation over time than minute ventilation; such as an acceleration sensor G internal to the case, or by a combination of the signals delivered by these two types of sensor. The reader is referred to European Patent Application EP-A-0 750 920 and its corresponding U.S. Pat. No. 5,722,996, and EP-A-0 770 407 and its corresponding U.S. Pat. No. 5,766,228, also assigned herewith to Ela Médical, for additional details regarding the minute ventilation sensor and the activity acceleration sensors as may be employed in the present invention.

Figure 2:
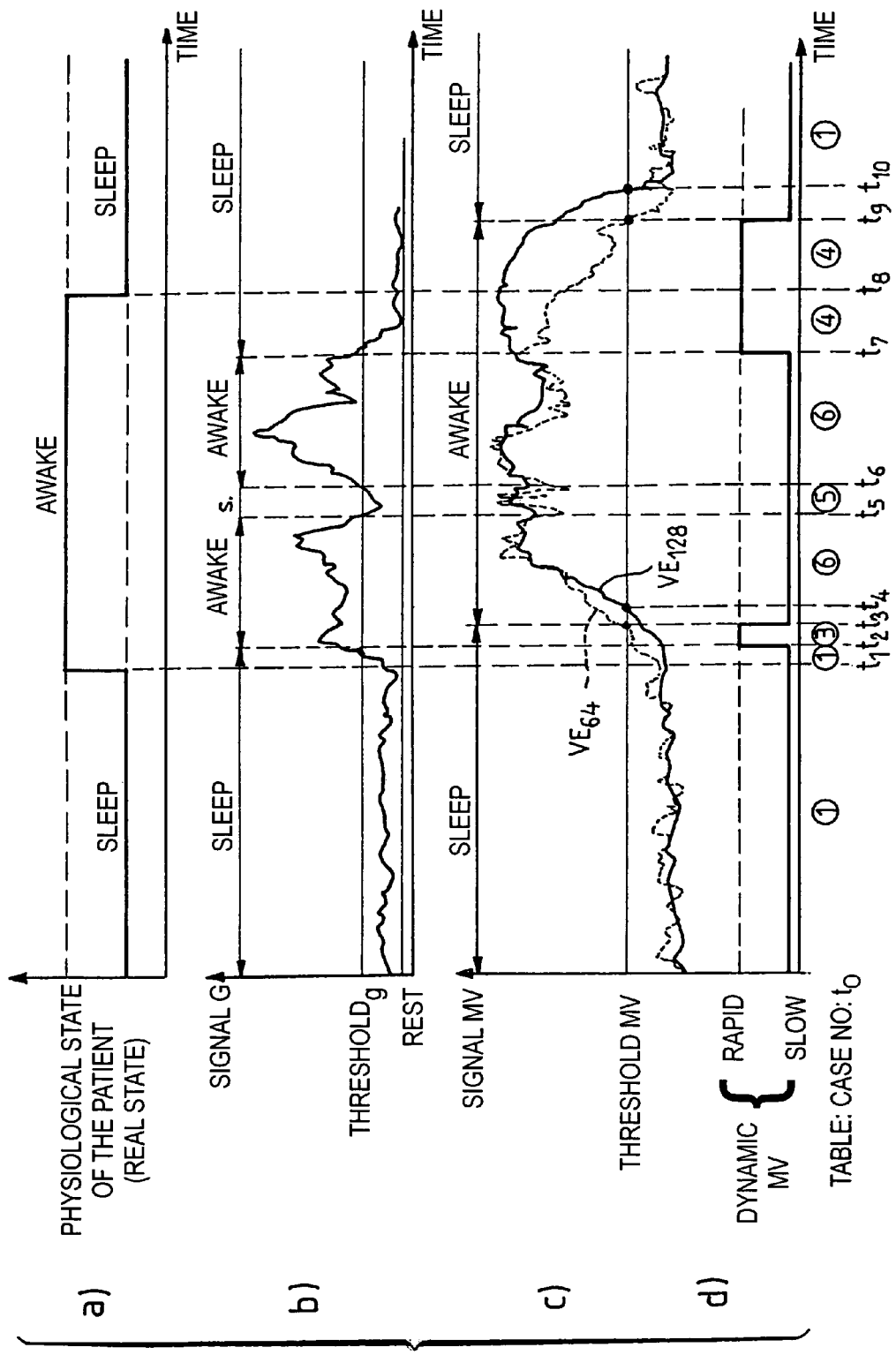
FIG. 2 is a series of chronograms explaining the way in which discrimination between awakening and sleep is operated in accordance with a preferred embodiment of the invention.

Regarding the determination of whether the patient is in a state of sleep or awakening, with reference to FIG. 2, the chronogram of line (a) represents the real physiological state of the patient, who is initially in a sleep phase (SLEEP). At the moment $t_1$ the patient awakens (AWAKE), and this awakening phase has a duration that ends at the moment $t_8$ when the patient enters a new sleep phase (SLEEP).

The chronogram of line (c) represents in full line the signal MV delivered by the minute-ventilation sensor MV, after the minute-ventilation measure was sampled and averaged over the 128 preceding respiratory cycles. This average value is indicated $VE_{128}$ The signal MV is a predominantly physiological parameter obtained by an intrathoracic impedance measurement. This measurement is preferably obtained between two electrodes laid out in the rib cage, or between an electrode (for example, a stimulation electrode, if the implanted device is a cardiac pacemaker) and the case of the device. The impedance is measured by the previously mentioned constant current injection Bonnet J L, et al.

A transition between awakening and sleep phases can be detected by comparing average value $VE_{128}$ with a threshold, indicated "Threshold MV", determined from an average value calculated over 24 hours of signal MV. Thus, in the illustrated example, the awakening of the patient was detected at the moment $t_4$ (reflecting a delay $t_4$-$t_1$ compared to the real moment of the awakening) and the falling-asleep at the moment $t_{10}$ (reflecting a delay $t_{10}$-$t_8$ compared to the real moment of falling asleep).

To reduce these delays in the detection of the phase shifts, it alternatively is proposed to use an auxiliary sensor, preferably and typically an acceleration sensor ("sensor G"). The signal delivered directly by the sensor G is then averaged over a relatively short duration (for example, 64 cardiac cycles) in order to eliminate artifacts and any short, non significant, variations. This averaged signal, indicated "signal G" is represented by the curve of the chronogram of the line (b) of FIG. 2. Signal G is then compared with an activity threshold, indicated "Threshold G", which, for example, is fixed at 10% above the value of the base line. The base line corresponds to a rest condition. If signal G exceeds Threshold G, one will define a state of the patient as being in an awakening phase according to the sensor G; in the contrary case, one will define the state as a sleep phase according to the sensor G. The device thus has two state indicators of awaking/sleep, defined starting from the two signals signal MV and signal G. These two states can be concordant or not.

The state of the patient being in an awakening or sleep phase continues to be diagnosed on the basis of signal MV but, according to the situation, the value having to be compared with Threshold MV will be either average $VE_{128}$ (referred to herein as the "slow dynamic") or average $VE_{64}$ calculated over a shorter period, typically over 64 preceding samples (referred to herein as the "fast dynamic").

The evolution of average $VE_{64}$ is illustrated in dotted lines on line (c) of FIG. 2, where one can see that the characteristic presents a form more variable than that of average $VE_{128}$ because the average taken over a shorter period has a larger variability. If the states (awake/sleep) given by the two signals, signal G and signal MV, agree, then the operation of the device is not modified, i.e., the state of awakening or sleep is given starting from signal MV by comparing $VE_{128}$ with Threshold MV (the slow dynamic).

On the other hand, in the event of discordance between the two signals (i.e., they do not produce the same phase), an additional criterion is introduced, which is the trend of the signal MV: decreasing, stable or increasing. This trend is determined by comparison between current value $VE_{128}$ and a value $VE_{128}$ previously calculated. The trend is known as stable if the variation is less than 10%, and otherwise it is deemed as increasing or decreasing, according to the sign of the variation.

When a change of state of the sensor G occurs, and the signal MV indicates an appropriate trend, the operation of the device is modified so as to determine the state as being in an awakening or sleep phase starting not from $VE_{128}$ (slow dynamic), but starting from $VE_{64}$ (fast dynamic) so as to get a greater reactivity. The cases where the dynamic is made fast are summarized by the state table below.

TABLE 1

| State Sensor MV | State Sensor G | Trend Signal MV | Dynamic | Case No. (FIG. 1) |
|---|---|---|---|---|
| Sleep | Sleep | — | Slow | 1 |
| Sleep | Awake | Decrease/Stable | Slow | 2 (not shown) |
| Sleep | Awake | Increasing | Fast | 3 |
| Awake | Sleep | Decreasing | Fast | 4 |
| Awake | Sleep | Increasing/Stable | Slow | 5 |
| Awake | Awake | — | Slow | 6 |

Referring to the example illustrated on Fig 2, initially the sensor MV indicates a sleep phase ($VE_{128}$, Threshold MV); as long as the sensor G confirms this phase, the dynamic remains slow. At moment $t_1$, the patient awakes, but none of the two sensors (MV, G) yet crossed a threshold defining a change of state.

At moment $t_2$ the awakening phase is diagnosed by the sensor G, and as the trend of signal MV is increasing, the analysis of signal MV passes to a fast dynamic: it is the signal $VE_{64}$ (and no more $VE_{128}$) that is then compared with Threshold MV.

When, at moment $t_3$ $VE_{64}$ reaches Threshold MV, the two sensors each indicate a state of awakening phase, which is thus confirmed as such to the device, and the dynamic becomes again slow.

At the time of the episode between moments $t_5$ and $t_6$, which can, for example, correspond to a period of short rest, the sensor G indicates a of sleep phase (signal G passes again below Threshold G) but $VE_{128}$ thus remains higher than Threshold MV. As a result, the device continues to consider the state to be awakening—and, trend MV not being decreasing, the dynamic remains unchanged (it remains slow).

The end of the awakening phase is characterized by a period of progressive rest of the patient that leads to the passing into the sleep phase at moment $t_8$. For this period of progressive rest, falling asleep is detected at moment $t_7$ by the sensor G, the trend MV signal being decreasing, and the dynamic becomes fast to be able to detect an apnea that could occur at the beginning of sleep, and being precise on the number of episodes. This fast dynamic is then maintained until confirmation of a sleep state, at moment $t_9$ by the sensor MV, corresponding to the crossing of Threshold MV by signal $VE_{64}$.

Ultimately, the detection of the awakening or sleep phases according to the invention makes it possible to advance the moment of detection of the awakening phase from $t_4$ (as obtained by the prior art) to $t_3$ (as obtained by the invention), and the detection of the sleep phase of $t_{10}$ (with the prior art) with $t_9$ (with the invention).

It will be noted that the use of signals $VE_{128}$ and $VE_{64}$ is not restrictive, and that it is equally possible to use signals $VE_{64}$ and $VE_{32}$ or $VE_{16}$, etc., in a comparable manner. In addition, it can be advantageous to envisage after each change of the dynamic a period of delay (for example, a duration of X respiratory cycles) or including a hysteresis loop, during which the dynamic is not modified, so as to avoid the undesirable phenomena of oscillations that might occur during changes of the dynamic.

The detection of the waking-up is used in the following way within the framework of the present invention. If a waking-up is detected within a short time (for example, 5 minutes) after the beginning of the acceleration of the heart rate by stimulation, then a counter of waking-ups is incremented. At the following sleep phase, if, again, the heart rate is increased by stimulation following detected hypopnea and this acceleration induces a waking-up under the same conditions as in the prior acceleration, previously, the waking-ups counter is again incremented. If the value of the waking-ups counter reaches a predetermined value, for example, five waking-ups, then the cardiac stimulation frequency target in response to a detection of hypopnea is reduced (i.e., modified in the reverse direction) by a step, for example, reduced by 5 beats per minute (bpm). The process is repeated and this reduction is operated in an iterative way until the increase in the heart rate becomes equal to 5 bpm (for example) above the spontaneous rate of the patient, because, if reduced further, such a low level of "increased stimulation" could be regarded as ineffective for therapeutic purposes.

Advantageously, the device also envisages to detect certain cases of false positives. Indeed, the sensors for the detection of oxygen desaturation, and in particular of the minute-ventilation, can present false positives. For example, for certain positions of the patient at the time of his sleep, because of a modification of the breathing, which becomes primarily abdominal and which can induce a significant reduction of the variations of thoracic respiratory volume, this can present a false positive. In this case, sensor MV would record—wrongly—phases of respiratory pauses, or hypopneas, presenting abnormally long durations, able to reach as long as several minutes. It is provided advantageously that, in this case, these particular episodes are excluded from the counting of the events likely to start a modification of the operating parameters of the device, because their duration exceeds a threshold, for example, a one minute threshold for the respiratory pauses, and a five minute threshold for hypopneas.

Suitable devices for which the present invention has application include, but are not limited to, for example, the CHORUS RM™, TALENT™ and SYMPHONY™ brands of implanted cardiac rhythm management devices available from Ela Médical, Montrouge, France. These devices are capable of receiving software instructions by telemetry, storing them in memory, and then executing those instructions to perform the functions described above in implementing the present invention, including the use of the minute ventilation signal acquired by the existing devices.

The circuits for sensing a minute ventilation signal and an acceleration signal comprises substantially all of logic and hardware elements required to operate the sensors to sense the associated parameter and produce output signals corresponding to the sensed parameters, and to deliver signals utilizable by the main circuit of the implant. The main circuit includes a microprocessor and memory (RAM and/or ROM), as well as conventional latches, registers and power supplies (not shown) for processing the output signals provided by the respective sensors. The creation of suitable software instructions for controlling a medical device, and in particular an implantable medical device, to perform the aforementioned functions of the present invention are believed to be within the abilities of a person of ordinary skill in the art.

Furthermore, the preferred embodiment of the invention described herein is implemented in an architecture including a microprocessor having associated software instructions stored in memory (ROM) and analog and digital logic circuits that are themselves known. Such an architecture is, for example, employed in the aforementioned devices manufactured by ELA Medical employing dual chamber cardiac pacing capabilities.

Although it does not present all of the advantages of the preferred solution with a microprocessor, a design in hard-wired discrete circuits having dedicated logic circuits is nevertheless perfectly foreseeable, and equally within the framework of the present invention.

One skilled in the art will appreciate that the present invention can be practiced by other than the described embodiments, which are presented for purposes of illustration and not of limitation.

The invention claimed is:

1. An active implantable medical device, comprising:
    means for measuring a respiratory activity of a patient having an output signal corresponding to ventilatory activity of the patient;
    means for analyzing the output signal of ventilatory activity and determining at regular intervals a measure of ventilatory activity;
    means for calculating a first sliding average of a first number of ventilatory activity measures;
    means for calculating a second sliding average of a second number of ventilatory activity measures, the second number of ventilatory activity measures being consecutive to said first number of ventilatory activity measures;
    means for determining a difference between the first and second sliding averages;
    means for detecting an occurrence of a hypopnea in response to said difference between the first and second sliding averages being between 50% and 100%;
    means for delivering cardiac stimulation pulses at a stimulation rate;
    means for modifying said stimulation rate, including means for increasing said stimulation rate in response to a first detected hypopnea; and
    means for detecting a phase of patient activity including an awakening phase and a sleep phase and a transition between said sleep and awakening phases, wherein the analyzing means further comprises means for comparing a modification of said stimulation rate and a detected transition from a sleep phase to an awakening phase and means for determining a correlation between said modification and said transitions and providing a correlation indicator indicative of a correlation between a modification of the operating parameter and consecutive transitions from a sleep phase to an awakening phase, and for delivering said correlation indicator in the event of a determined correlation.

2. The device of claim 1, wherein the analyzing means further comprises means for delivering said correlation indicator in the event of an occurrence of a transition during a given time interval following a modification of the stimulation rate.

3. The device of claim 1, wherein the means for modifying the stimulation rate further comprises a means for modifying in a reverse direction said modified operating parameter in response to a provided indicator of correlation by the analyzing means.

4. The device of claim 3, wherein the means for modifying the stimulation rate in the reverse direction further comprises means for counting delivered correlation indicators and means for modifying said stimulation rate in the reverse direction when the count of delivered correlation indicators is greater than a predetermined level.

5. The device of claim 3 wherein the means for modifying the stimulation rate in the reverse direction further comprises means for decreasing said stimulation rate to a rate that is greater than or equal to a base rate.

6. The device of claim 1, wherein the means for determining a ventilatory activity measure at regular intervals further comprises means for calculating said ventilatory activity measure during a predetermined time interval.

7. The device of claim 1, wherein the means for determining a ventilatory activity measure at regular intervals further comprises means for calculating said ventilatory activity measure during a respiratory cycle and said first number is a non-zero integer number N', and said second number a non-zero integer number N, wherein N and N' are a predetermined number of respiratory cycles.

8. The device of claim 1, wherein the analyzing means further comprises:
    means for determining a duration of hypopnea in response to an occurrence of a first hypopnea.

9. The device of claim 8, wherein the analyzing means further comprises means able to discriminate a respiratory pause phase from a hypopnea phase, and suspend the determination of the duration of hypopnea during a respiratory pause phase.

10. The device of claim 8 wherein the means for determining the duration of hypopnea further comprises:
    means for counting a number of consecutive respiratory cycles for which the average of the ventilatory signal of activity remains lower than a predetermined threshold of comparison of the last non-hypopneic average.

11. The device of claim 8 wherein the means for determining the duration of hypopnea further comprises:
    means for counting a number of periods of calculation of the first and second sliding averages for which the calculated average of the ventilatory activity signal remains below a predetermined threshold of comparison of the last non-hypopneic average.

12. The device of claim 1 wherein the analyzing means further comprises means for determining a duration of hypopnea in response to an occurrence of a first hypopnea, wherein the control means further comprises means for modifying an operating parameter in response to an accumulated duration of hypopneas measured over a given period being greater than a predetermined threshold.

13. The device of claim 1 wherein the analyzing means further comprises:
    means for determining a duration of hypopnea in response to an occurrence of a first hypopnea; and
    the control means further comprises means for modifying said stimulation rate in response to the count of hypopneas measured over a given period being greater than a predetermined threshold.

14. The device of claim 1 wherein the stimulation rate is accelerated to achieve an increase from about 15 to about 20 beats per minute in the patient.

15. The device of claim 1 wherein the stimulation rate is accelerated to achieve an increase of about 20% of the spontaneous cardiac rate in the patient.

* * * * *